(12) United States Patent
Paschke

(10) Patent No.: US 9,018,887 B2
(45) Date of Patent: Apr. 28, 2015

(54) ULTRASONIC SYSTEM CONTROLS, TOOL RECOGNITION MEANS AND FEEDBACK METHODS

(75) Inventor: Richard H. Paschke, Timonium, MD (US)

(73) Assignee: Westdale Holdings, Inc., Timonium, MD (US)

(*) Notice: Subject to any disclaimer, the term of this patent is extended or adjusted under 35 U.S.C. 154(b) by 909 days.

(21) Appl. No.: 13/078,134

(22) Filed: Apr. 1, 2011

(65) Prior Publication Data

US 2011/0241576 A1    Oct. 6, 2011

Related U.S. Application Data

(60) Provisional application No. 61/319,922, filed on Apr. 1, 2010.

(51) Int. Cl.
    *H02P 25/06*      (2006.01)
    *A61C 17/20*      (2006.01)
    *B06B 1/02*      (2006.01)
    *B06B 1/08*      (2006.01)

(52) U.S. Cl.
CPC ............... *A61C 17/20* (2013.01); *B06B 1/0253* (2013.01); *B06B 1/08* (2013.01)

(58) Field of Classification Search
CPC ............ A61B 17/320068; A61B 2017/00398; A61C 17/20; B06B 1/08; H01L 41/12; H01L 41/20
USPC .......................................... 318/119, 135, 687
See application file for complete search history.

(56) References Cited

U.S. PATENT DOCUMENTS

| | | | |
|---|---|---|---|
| 3,654,540 A * | 4/1972 | Honig et al. | 318/118 |
| 3,727,112 A | 4/1973 | Popescu | |
| 4,063,557 A * | 12/1977 | Wuchinich et al. | 604/22 |
| 4,184,092 A | 1/1980 | Wieser | |
| 4,331,422 A | 5/1982 | Heyman | |
| 4,820,152 A | 4/1989 | Warrin et al. | |
| 4,965,532 A | 10/1990 | Sakurai | |
| 4,973,876 A | 11/1990 | Roberts | |
| 5,013,241 A | 5/1991 | von Gutfeld et al. | |
| 5,139,509 A * | 8/1992 | Fischer et al. | 606/107 |
| 5,378,153 A | 1/1995 | Giuliani et al. | |
| 5,425,704 A | 6/1995 | Sakurai et al. | |

(Continued)

FOREIGN PATENT DOCUMENTS

WO     WO 85/02106     5/1985

OTHER PUBLICATIONS

International Search Report from PCT/US08/71511.

(Continued)

*Primary Examiner* — Bentsu Ro
(74) *Attorney, Agent, or Firm* — Carter DeLuca Farrell & Schmidt LLP

(57) ABSTRACT

An ultrasonic electro-mechanical resonant system and instrument that provides improvements in the design and implementation of a feedback system. The disclosed configuration and orientation of coils enhance the motional or velocity feedback signals while minimizing the effects of transformer coupling. A two coil and a three coil approach is disclosed that takes advantage of non-homogeneous magnetic fields. An asymmetrical arrangement enables velocity signals to be coupled into the coils without requiring additional signal conditioning or capacitive elements.

18 Claims, 4 Drawing Sheets

(56) References Cited

U.S. PATENT DOCUMENTS

| | | |
|---|---|---|
| 5,451,161 A | 9/1995 | Sharp |
| 5,733,281 A | 3/1998 | Nardella |
| 5,739,724 A | 4/1998 | Alexandre et al. |
| 5,754,016 A | 5/1998 | Jovanovic et al. |
| 5,819,027 A | 10/1998 | Budelman et al. |
| 5,880,580 A | 3/1999 | Johansen |
| 5,884,350 A | 3/1999 | Kurze |
| 5,897,569 A | 4/1999 | Kellogg et al. |
| 5,938,677 A | 8/1999 | Boukhny et al. |
| 5,959,390 A | 9/1999 | Boukhny |
| 6,019,775 A | 2/2000 | Sakurai |
| 6,028,387 A | 2/2000 | Boukhny |
| 6,175,180 B1 | 1/2001 | Angelini et al. |
| 6,190,167 B1 | 2/2001 | Sharp |
| 6,227,853 B1 | 5/2001 | Hansen et al. |
| 6,241,520 B1 | 6/2001 | Gofman et al. |
| 6,503,081 B1 | 1/2003 | Feine |
| 6,545,390 B1 | 4/2003 | Hahn et al. |
| 6,577,642 B1 | 6/2003 | Fijolek et al. |
| 6,819,027 B2 | 11/2004 | Saraf |
| 7,269,873 B2 | 9/2007 | Brewer et al. |
| 7,614,878 B2 * | 11/2009 | Paschke et al. ............... 433/119 |
| 2003/0222535 A1 | 12/2003 | Gofman et al. |
| 2005/0142515 A1 | 6/2005 | Levy et al. |
| 2005/0227201 A1 | 10/2005 | Pond |
| 2007/0166663 A1 | 7/2007 | Telles et al. |

OTHER PUBLICATIONS

International Search Report from PCT/US06/19201.

* cited by examiner

ULTRASONIC SYSTEM CONTROLS, TOOL RECOGNITION MEANS AND FEEDBACK METHODS

This application claims the benefit of priority to U.S. Provisional Application Ser. No. 61/319,922 entitled "ULTRASONIC SYSTEM CONTROLS, TOOL RECOGNITION MEANS AND FEEDBACK METHODS", filed Apr. 1, 2010 by Richard H. Paschke, the entirety of which is incorporated by reference herein for all purposes.

BACKGROUND

1. Technical Field

The present disclosure relates to ultrasonic electro-mechanical resonant systems. More specifically, the present disclosure relates to improvements in the design and implementation of a feedback system employing the configuration and orientation of coils that enhance the effects of motional or velocity feedback signals and minimize the effects of transformer coupling.

Additionally, the present disclosure relates to a detection system to determine the impedance or inductance of a tool placed in an ultrasonic handpiece. This system includes the ability to differentiate or select tool characteristics prior to and after activation.

2. Background of Related Art

In general, magnetostrictive, electro-mechanical resonant systems are driven by applying an AC signal to a coil that activates a magnetic or ferro-magnetic member, hereinafter referred to as a transducer, by creating a magnet field. The resultant magnetic field creates compressional or standing waves in the transducer, causing it and parts connected thereto to vibrate. The aggregate assembly of the transducer and connected parts, which are hereinafter referred to as tools, are typically supported at nodal points of the longitudinal motion to minimize any loss of motion or kinetic energy of the vibrating tool. The energy created in the vibrating tool may be applied in performing ultrasonic machining, welding, cleaning, dental calculus debridement, or other applications. It is desirable to operate the tool with maximum amplitude of vibration at the working end of the tool. This is achieved when the drive signal is at one of the frequencies of resonance of the transducer or tool.

The desired frequency of resonance is affected by wear, tool geometry, operational temperature, and loading of the tool. To maximize the utility of the tool, the operational frequency of the system drive should be capable of varying in response to the dynamic tool resonance conditions.

Currently produced ultrasonic systems that use some form of feedback to control the drive frequency are limited by a multitude of compromises. The following are some examples of these compromises.

Systems that use the current and voltage characteristics in the drive circuits typically simulate a motional characteristic at a single operating point and use its value for all drive levels.

Most feedback systems that employ a feedback coil near the free end of the transducer to detect the velocity or motion of the transducer use a few turns of reverse drive winding to minimize the transformer coupling effects. This poses several problems. Such reverse winding require the drive levels to be higher than otherwise required because the reverse winding subtracts from the total drive signal. Additionally, the feedback winding needs to be isolated from the end of the drive winding by adding a gap between the windings. Shortening the length of the drive winding limits the total length of the driving magnetic field. The number of turns on the reverse winding is critical because they affect the phase relationship between the drive and feedback signals.

Systems that employ two symmetrical windings wound in reverse magnetic sense are position sensitive, which is in part due to the non-homogeneity of the drive field. These systems are also sensitive to nodal point positioning of transducers with systems using interchangeable tools. This configuration of feedback typically requires some form of post feedback signal conditioning which modifies the phase information, and/or requires the addition of a capacitor across the winding(s).

Some ultrasonic systems provide the option of interchangeable tools. The performance of these tools can vary as a result of certain parameters of the tools. If the impedance varies, for example, corrections could be made to the performance with knowledge of the parametric value. In another instance, a system may have removable tools that provide fundamentally different operations such as ultrasonic vibration and induction heating.

Currently available systems typically use voltage or current levels and frequency or phase information in conjunction with logic circuits that interpret the values. For example, Karnaugh maps or similar Boolean operations are used to select one operational mode or the other. Inherent limitations associated with these prior art systems are that these inputs are often ambiguous due to the effects of manufacturing variations in the tools and operational variations during tool loading.

The present disclosure takes advantage of the non-homogeneous magnetic fields and has been successfully modeled and works without additional signal conditioning. It is the asymmetry of the two coil configuration that makes the difference, with the three coil configuration producing the best results.

SUMMARY

In accordance with one embodiment of the present disclosure, a configuration of three coils, wherein the winding direction of the two distal coils are in the same direction, and a center coil that is wound in the opposite direction from the distal coils. In a preferred configuration, the sum of the windings of the two distal coils equals the number of windings of the center coil. The spacing between the two distal coils relative to the center coil may be symmetrical or asymmetrical. In some cases a small number of additional turns may be added to the distal coils to compensate for the effects of a non-homogeneous magnetic field as the position of the distal coils approach the ends of the drive coil. Another effect that results in inducing voltage into the feedback coils is the changing permeability of the vibrating transducer. A relatively symmetric dynamic stress pattern exists along the length of the transducer with the maximum effect located in the nodal region. This configuration minimizes the effects of transformer coupling between the drive and feedback coils.

The effect of the pick-up configurations above are further enhanced by addition of a gap in the drive windings. The two sections of the winding are continuous and wound in the same direction including at least one gap at a distal position of the coil. Removing a number of turns in the drive winding in this manner produces a field correction that acts to depress the induced transformer voltages in the feedback coils.

Another embodiment comprises an asymmetrical two coil configuration with the coils wound in opposite directions. In one configuration, the coils are on opposite sides of the transducers nodal region. The spacing between the coils is determined in part by the length of the transducer and the centerline of the spacing between the coils can be positioned about the nodal region to increase the motional feedback effect. The larger coil can be placed on either side of the nodal region with the preferred position being the one producing the greatest induced motional feedback voltage. This configuration also provides a minimization of the transformer coupling by means of the opposite sense of the windings and the asymmetry of the windings. The feedback signal is generated at least in part by the summation of the induced motional or velocity signals in the feedback coils. The asymmetry of the coils also enhances the motional feedback signal based on the non-homogeneity of the drive field.

An aspect of this disclosure includes determining the impedance or inductance of a transducer placed in the handpiece. In one embodiment, a bridge circuit is configured to have one leg connected to the drive coil such that it has minimum affect on the operation of the handpiece, drive system or feedback. A suitable stable oscillator is placed across the bridge and an ancillary circuit is connected in quadrature to the oscillator. The output of the bridge is balanced or nulled with a standard tool in place. The nulling operation can be done once during alignment of the circuit, e.g., during testing, at predetermined intervals during normal operation, upon application of power to the drive circuit, or whenever the drive circuit is not activated depending on the application. The null value can then be stored or otherwise processed so that its value can be used as a comparison value when another transducer or tool is placed in the handpiece. The circuit parameters can also be adapted to allow nulling of the circuit when no tool is in the handpiece. In this way, the detection circuit can provide a means to limit power to the handpiece when no transducer is present.

An ancillary circuit can be a simple operational amplifier or a series of amplifiers, signal conditioning circuits or buffer stages that produce the desired output characteristics. A linear voltage curve proportional to the value of the transducer or tool inductance is a non-limiting example. It is envisioned that the circuitry described is capable of tracking changes in the inductance from uH to mH ranges.

Current ultrasonic systems have inherent limitations in their ability to capture and lock onto transducers due to manufacturing tolerances of transducer inductance. A transducer outside a specific range of inductance often results in the failure of the electronics to operate the tool, which is in part due to phase shifts outside the normal operating limits of the system. The proposed disclosure has the ability to detect the transducer inductance and apply a correction or change to the oscillator circuit's operational parameters, which allows the system to function normally.

A further embodiment of this disclosure is a means to optimize transducer performance, control the operational power range of the tool, or alert the operator that the transducer has been damaged through handling. A common cause for the transducer to lose inductance is due to work hardening the magnetostrictive material. For example, dropping a transducer a height of 4 feet can result in a 3% loss of initial inductance. Even slight deformation of the transducer due to handling and re-straightening the transducer can result in a 10% to 15% loss in inductance.

BRIEF DESCRIPTION OF THE DRAWINGS

Various embodiments of the presently disclosed control, feedback and detection circuits are described herein with reference to the drawings wherein.

DETAILED DESCRIPTION

Particular embodiments of the present disclosure are described hereinbelow with reference to the accompanying drawings. In the following description, well know functions or constructions are not described in detail to avoid obscuring the present disclosure in unnecessary detail.

Figure 1:
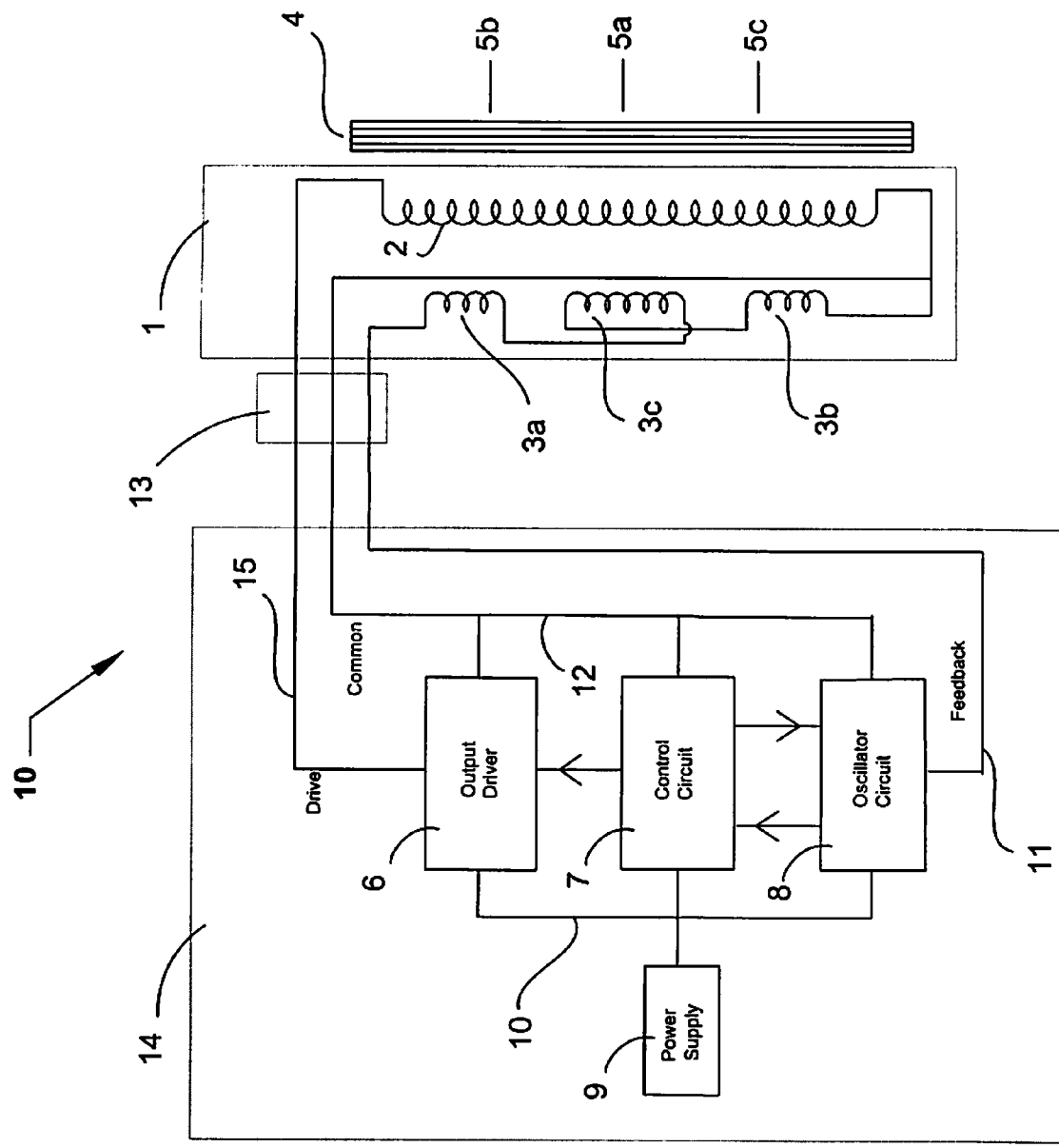
FIG. 1 is a view of a three-coil feedback system connected to a dental scaler system in accordance with one embodiment of the present disclosure.

Turning now to FIG. 1, disclosed is a dental scaler system 10 including a dental scaler device 14, and a handpiece 1 that is operatively coupled to the dental scaler device 14 via a cable 13. The dental scaler device 14 includes a power supply 9, which may be either internal or external to the dental scaler device 14, an oscillator circuit 8, a control circuit 7, and an output driver 6. The power supply 9 provides one or more voltages to the scaler device 14. The one or more voltages provide input to the scaler device 14 (e.g., indicator lights) and its oscillator circuit 8, control circuit 7, and output driver 6, which in combination convert the DC voltage into high frequency signals for driving the handpiece 1 and provide power to process the feedback and control signals.

The handpiece includes an energizing coil 2, and feedback coils 3a, 3b, and 3c, which in combination provide a signal via feedback line 11 to control the oscillator circuit 8. In the example shown, the sense of the drive coil 2 winding is counter clockwise. The feedback coils 3a and 3b are wound in a clockwise sense, and feedback coil winding 3c in a counterclockwise sense. When wound in this configuration, the coupled signal induced by transformer action of the handpiece with a transducer 4 inserted into the handpiece 1 is minimized and the signal induced by the motion of the activated transducer, also referred to as velocity feedback is predominant. Although the transducer 4 is shown as a laminated component, a solid transducer or a ferromagnetic transducer or other suitable construction may be utilized. Those skilled in the art will recognize that the sense of the feedback coils 3a and 3b may also be wound in a counterclockwise sense and the feedback coil 3c wound in a clockwise sense.

In one embodiment, the number of windings in feedback coil 3c is slightly smaller than the sum of the windings for feedback coils 3a and 3b due to the smaller transformer coupling effect near the ends of the stack. In practice, the total length of the coils 3a, 3b, and 3c, including the spacing between the coils, should be approximately ⅔ the length of the drive coil.

By placing feedback coil 3c in the nodal region 5a and feedback coils 3a and 3b near the loops of vibration 5b and 5c, the combination of feedback coils 3a, 3b, and 3c, become less sensitive to the axial displacement of transducer 4. In a preferred embodiment, the configuration provides placement of the feedback coils 3a, 3b, spaced a distance from the ends of the drive coil 2 to minimize the effects of non-homogeneities of the magnetic field.

Continuing with reference to FIG. 1, the oscillator circuit 8, which in the case of a phase lock circuit, would begin sweeping its frequency either up or down from a nominal starting point until the transducer 4 begins to vibrate. As the vibrations build, the oscillator circuit 8 approaches the transducer 4 frequency of resonance, the feedback 11 is input to the oscillator circuit 8 via handpiece connector 13 and reinforces the vibration of the transducer 4 wherein the oscillator circuit 8 locks onto the operational frequency of the transducer 4. The output of the oscillator circuit 8 is connected to control circuit 7, which processes the signal and couples it to the output driver 6. The signal of output driver 6 is connected via handpiece cable 13 to the handpiece 1 of the dental scaler system 10, which provides the power to drive the transducer 4. The common handpiece lead 12 for the drive coil 2 and feedback coils 3a, 3b, and 3c, the drive 15 and feedback 11 are connected via handpiece cable 13 to the oscillator circuit 8, control circuit 7, and output driver 6 of the dental scaler device 14 as shown.

Figure 2:
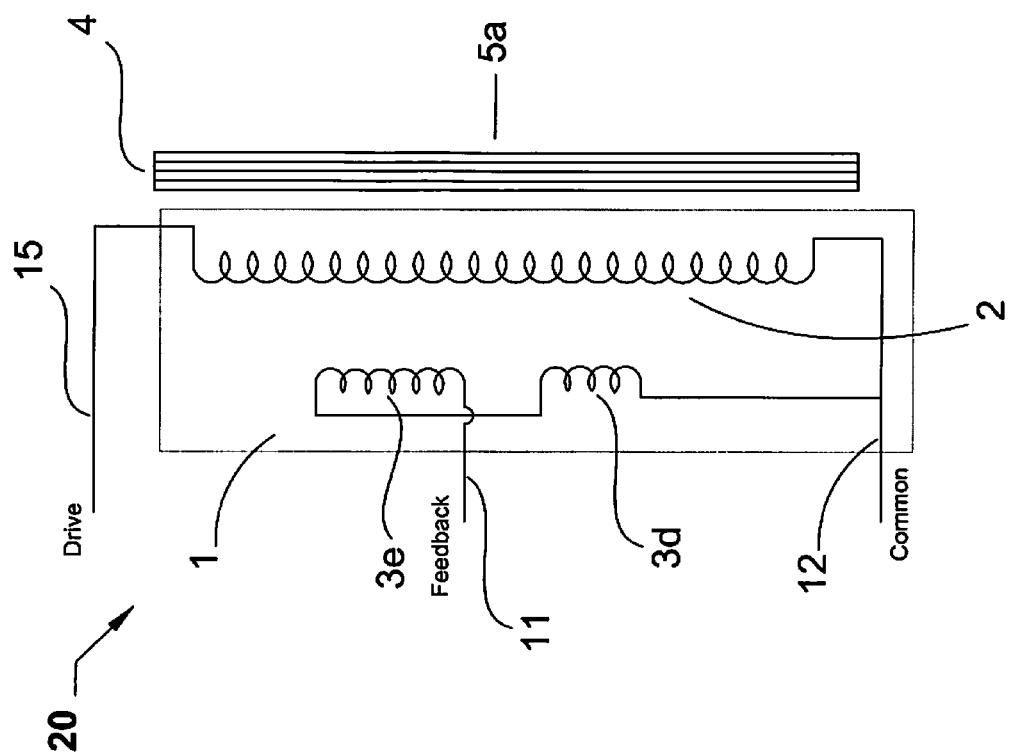
FIG. 2 is a view of a two-coil feedback system in accordance with an embodiment of the present disclosure.

Turning now to FIG. 2, which shows an alternate handpiece configuration wherein feedback coils 3d and 3e, are in an asymmetrical arrangement. Feedback coil 3e has a greater number of turns than feedback coil 3d. In a preferred embodiment, the ratio of turns for feedback coils 3d and 3e is 1.25, and the total length of the coils including the spacing between coils is approximately ⅔ the length of drive coil 2. This configuration is further differentiated from the configuration shown in FIG. 1 by placement of the feedback coils 3d and 3e with reference to the nodal region 5a of transducer 4. Feedback coils 3d and 3e are positioned to minimize the effects of transformer coupling from the drive coil 2, with the spacing between the coils positioned in the nodal region 5a, during operation. It is envisioned that the position of feedback coils 3d and 3e may be reversed such that the signal obtained for the motional component of the activated transducer 4 is maximized. Alternate handpiece configuration 20 is connected to dental scaling system 10 in the same manner as disclosed hereinabove.

Figure 3:
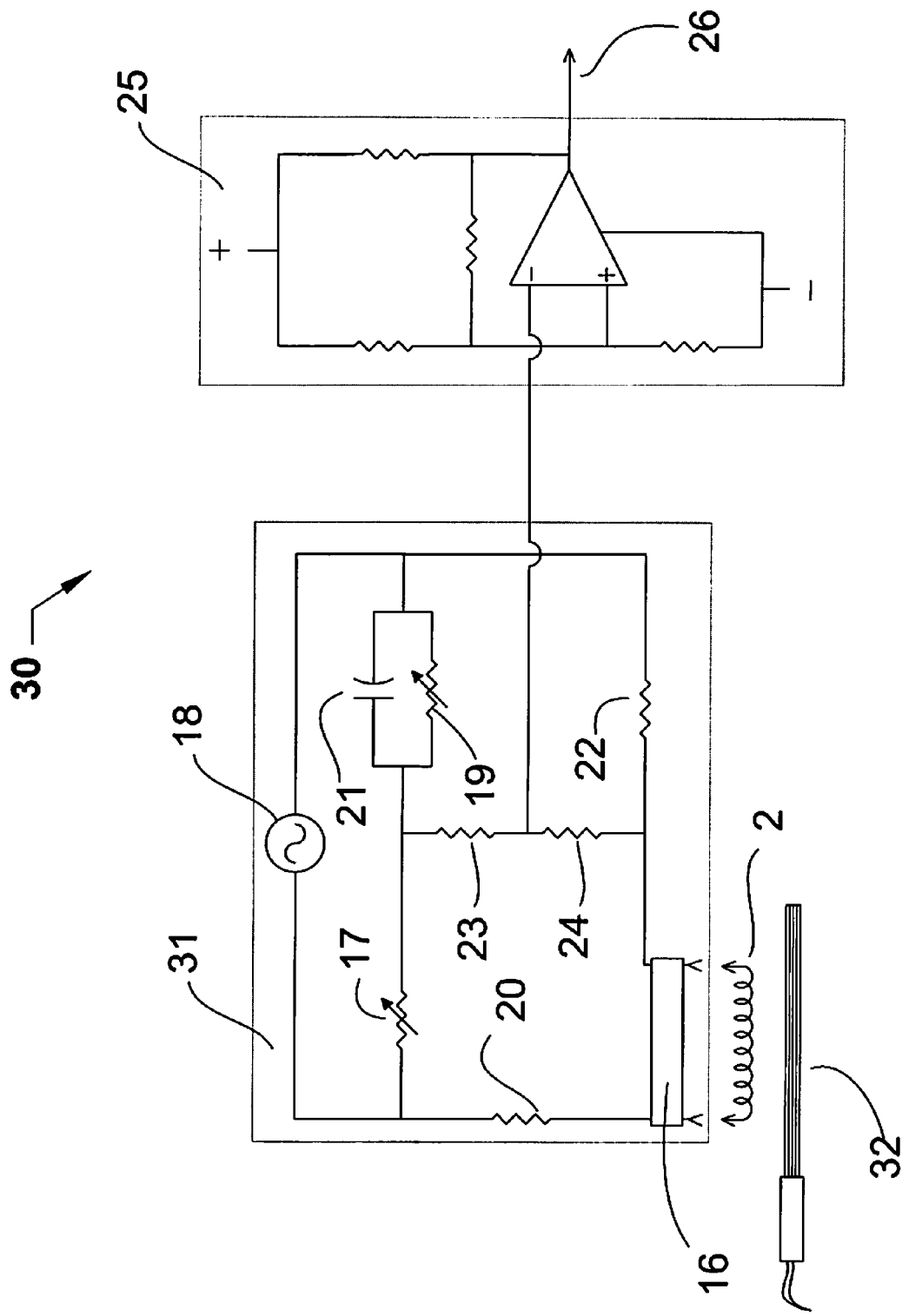
FIG. 3 is a schematic diagram of a control circuit in accordance with an embodiment of the present disclosure.

Referring now to FIG. 3, the control circuit 30 includes a detection circuit 31, wherein the value of the inductance of an operational tool 32 is determined by comparing the output 26 of the tool 32 to a value obtained during calibration of a standard transducer 4. For example, and without limitation, the inductance range for a typical dental scaler system 30 may be 260 to 340 uH for a 30 kHz system and 340 to 460 uH for a 25 kHz system. By definition, a standard transducer for the 30 kHz system would be 300 uH and 400 uH respectively for a 30 kHz and a 25 kHz system. The calibration or nulling operation may be performed with a standard transducer 4 placed in handpiece 1, with the dental scaler system 10 with its ultrasonics either activated or not activated, as described in detail below.

With continuing reference to FIG. 3, a typical detection circuit 31 is shown with a frequency source 18, fixed bridge resistors 20, and 22, fixed bridge capacitor 21, and adjustable bridge resistors 17 and 19. Fixed bias resistors 23 and 24 are selected as required by the ancillary circuit 32 to achieve an acceptable null value at output 26. It is envisioned that the capacitive reactance in the detection circuit 31 will exactly oppose the inductive reactance of the transducer 4 when the circuit is in balance (null position), allowing the value of the transducer 4 resistance $R_S$ and inductance $L_S$ (not explicitly shown) to be reliably determined. In general, the values of the fixed bridge components 20, 21, and 22 are known, and the variable components 17 and 19 are adjusted until the bridge is in balance (nulled). The values of $R_S$ and $L_S$ can be determined based the value of the other components. For an example without limitation, $L_S$ equals the product of the value of fixed resistor 22, times the value of adjusted variable resistor 17, times the value of fixed capacitor 21. $R_S$ equals the value of the product of the value of fixed resistor 22, times the value of adjusted variable resistor 17, divided by the adjusted value of variable resistor 19, minus the value of fixed resistor 20. Applying the above formulae, calculates the values for components 17, 19, 20, 21, 22 with component 18 at 30 kHz with a standard transducer 4 measuring 300 uH as respectively; 19.4 kilo Ohms, 28.9 kilo Ohms, 2.2 kilo Ohms, 0.093 micro Farads, and 3.3 kilo Ohms.

In further detail, calibration may be performed when the ultrasonics tool 32 is not activated, e.g., the level of drive line 15 is at the same level as common line 11 and no current is flowing in drive coil 2. A transducer 4 is placed in the handpiece 1. The power to the dental scaler system 10 is on, but the ultrasonic circuits are not activated. The purpose of calibration is to provide a decision point for the control circuits. The drive coil 2 is connected to bridge circuit 31 via interface 16. It is envisioned that the interface 16 may comprise a direct connect of both leads on drive coil 2, a direct connection of a single lead and a capacitive coupling on the second lead of drive winding 2, or a mechanical or solid state relay connection on one or both leads of drive coil 2. A transducer 4 with a predetermined value of inductance, for example 290 uH, is placed into handpiece 1. The null position 1 is achieved by varying adjustable resistors 17 and 19, in combination until output 26, is at zero volts as shown on curve 29, FIG. 4 by the intersection of the horizontal line, shown at a zero null 33, and the vertical inductance line 28, shown for standard transducer 4, FIG. 1. At the point where curve 29 is generated by the range of measured inductance values. For an example, and without limitation curve 29 would be generated by measurement of inductance values of tool 32 ranging from 260 to 340 uH for 30 kHz operation.

It is envisioned that for detection and measurement of high Q inductances of the transducer 4, components 19 and 21 may be placed in series rather than in parallel as shown in detection circuit 31.

Figure 4:
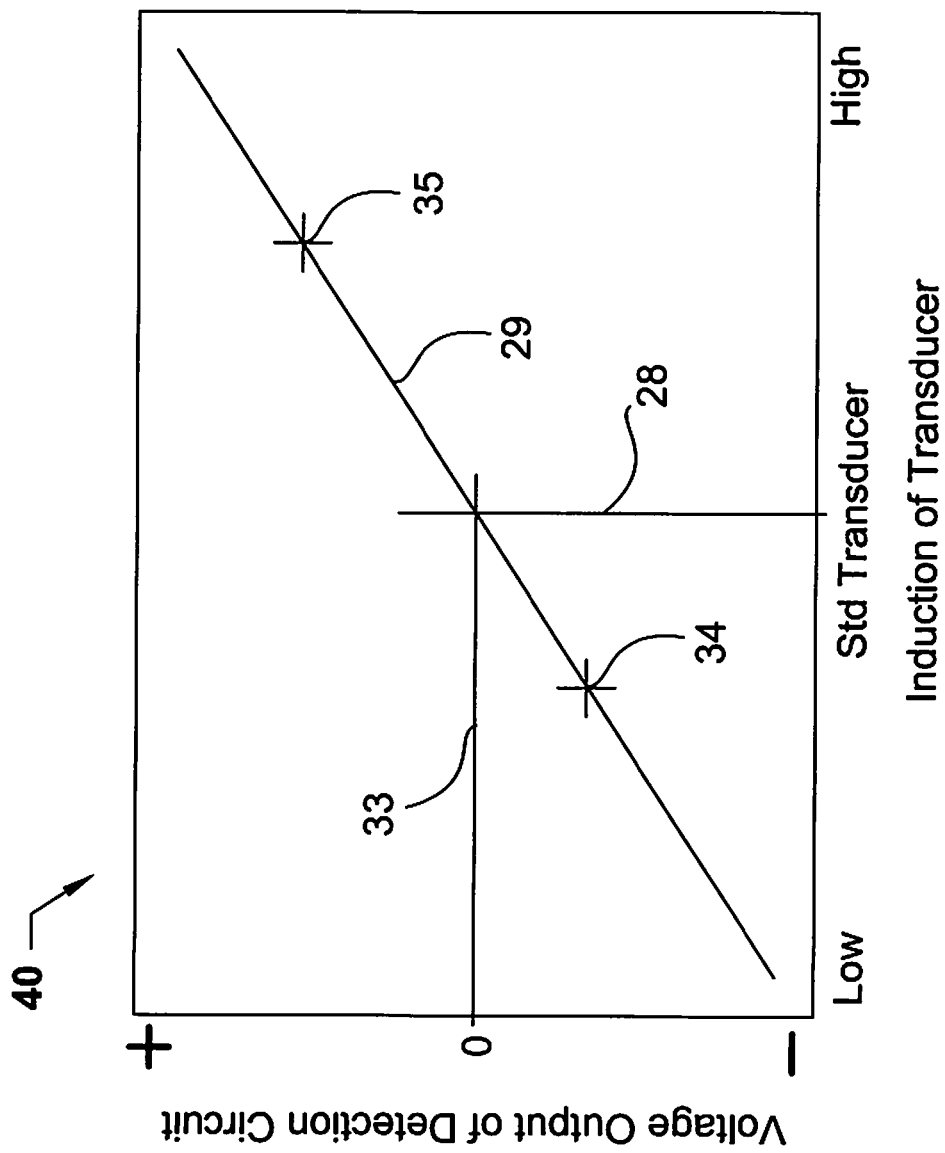
FIG. 4 is a graph of a linear output of a detection circuit in accordance with the present disclosure.

Now with reference to FIG. 4, the null condition is shown on control graph 40 as the intersection of the zero null voltage 33 (horizontal line) and the inductance line 28 representing the inductance value of a standard transducer 4 (vertical line). Replacing the standard transducer 4 with tool 32 whose inductance is in the range of 260 uH to 340 uH, for a 30 kHz system, thereby producing curve 29. It is envisioned that other points on the curve 29 can also be used as a null point by changing the bias conditions in the ancillary circuit 25. The output 26, of the ancillary circuit 25 for any tool 32, whose inductance deviates from the stand transducer 4 inductance of 300 uH, represents an error voltage. This error voltage is represented on output curve 26 as a point 34 whose inductance is lower than 300 uH and point 35, whose inductance is greater than 300 uH.

While output graph 40 shows a linear output curve 29, a non-linear output curve may be substituted in the case where, for example, a non-linear output would be better suited to provide an expanded control range for control circuit 7. It is well known in the art that a simple combination of bipolar transistors and operational amplifiers can be configured to convert linear signals into non-linear signals.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodi-

What is claimed is:

1. An ultrasonic magnetostrictive system, comprising:
an oscillator configured to provide electrical signals including a current signal and a voltage signal;
a drive circuit operably coupled to the oscillator and configured to amplify the electrical signals to generate a drive signal;
a handpiece operably coupled to the drive circuit and configured to operably engage a removable transducer, the handpiece including:
a drive coil configured to establish an electromagnetic field for driving the transducer; and
a feedback configuration, including:
a center coil having n turns wound in a first direction and having a portion of the center coil positioned in the nodal region of the transducer; and
at least one distal coil having greater than n turns, wound in a second direction opposite the first direction,
wherein the feedback configuration provides frequency and phase information regarding the transducer and minimizes the effect of transformer coupled signals.

2. The ultrasonic magnetostrictive system in accordance with claim 1, wherein the feedback configuration includes at least two distal coils, wherein a number of turns of each distal coil is n/2+i turns, wherein i is in a range of 0 turns to n/2 turns, and where i increases as a position of the at least two distal coils approaches an end of the drive coil, and wherein a length of the feedback configuration is less than a length of the drive coil.

3. The ultrasonic magnetostrictive system in accordance with claim 1, wherein a space between the center coil and the at least one distal coil is positioned in the nodal region of the transducer, wherein the at least one distal coil includes n+i turns, wherein i is in a range of 1 to n/2 turns, and where i increases as the position of the distal coil approaches an end of the drive coil, and wherein a length of the feedback configuration is less than a length of the drive coil.

4. The ultrasonic magnetostrictive system in accordance with claim 1, wherein the drive coil is continuously wound in a single direction and contains at least one gap in its windings.

5. A handpiece configured to operably engage a removable ultrasonic tool, the handpiece comprising:
a drive coil configured to establish an electromagnetic field for driving a transducer; and
a feedback configuration having a centerline and including:
a center coil having n turns wound in a first direction, at least a portion of the center coil positioned in a nodal region of the transducer; and
at least one distal coil, having greater than n turns, wound in a second direction opposite the first direction,
wherein the feedback configuration provides frequency and phase information regarding the transducer and minimizes the effect of transformer coupled signals.

6. The handpiece in accordance with claim 5, wherein the centerline of the feedback configuration is positioned in the nodal region of the transducer, and wherein the at least one distal coil includes n/2+i turns, wherein i is in a range of 0 to n/2.

7. The handpiece in accordance with claim 5, wherein the centerline of the feedback configuration is positioned between the nodal region and a loop region of the transducer.

8. The handpiece in accordance with claim 5, wherein the at least one distal coil in the feedback configuration includes n+i turns, wherein i is greater than 1, and wherein i increases as a distal end of the at least one distal coil approaches an end of the drive coil, and wherein a length of the feedback configuration is less than a length of the drive coil.

9. The handpiece in accordance with claim 5, wherein the feedback configuration includes at least two distal coils, wherein the number of turns on each distal coil is n/2+i turns, wherein i is in a range of 0 and n/2 turns, and wherein i increases as positions of the at least two distal coils approach an end of the drive coil, and wherein a length of the feedback configuration is less than a length of the drive coil.

10. The handpiece in accordance with claim 5, wherein the at least one distal coil in the feedback configuration includes n+i turns, wherein i is greater than 1, and wherein i increases as a distal end of the at least one distal coil approaches an end of the drive coil, wherein a length of the feedback configuration is less than a length of the drive coil, and wherein the at least one distal coil is positioned towards a free end of the transducer.

11. The handpiece in accordance with claim 5, wherein the drive coil is continuously wound in a single direction and contains at least one gap in its windings.

12. An ultrasonic magnetostrictive system, comprising:
a drive circuit configured to generate a drive signal;
a drive coil configured to receive the drive signal and establish an electromagnetic field for driving a transducer;
a feedback configuration, including:
a center coil having n turns wound in a first direction and having a portion of the center coil positioned in the nodal region of the transducer; and
at least one distal coil having greater than n turns, wound in a second direction opposite the first direction,
wherein the feedback configuration provides frequency and phase information regarding the transducer and minimizes the effect of transformer coupled signals; and
a control configuration, including:
an impedance detection circuit including a bridge circuit having at least one adjustable leg and at least one non-adjustable leg, wherein at least one of the adjustable legs is configured to balance an impedance of the transducer, wherein at least one of the adjustable legs includes a parallel combination of a resistor and a capacitor, and wherein the drive coil is operably coupled to the bridge circuit in a leg opposite the leg containing the capacitor; and
an amplifier configured to convert the output signal of the bridge circuit into a series of voltage values proportional to the impedance of the transducer.

13. The ultrasonic magnetostrictive system in accordance with claim 12, wherein a centerline of the feedback configuration is positioned in a nodal region of the transducer, and wherein the at least one distal coil includes n/2+i turns, wherein i is in a range of 0 to n/2.

14. The ultrasonic magnetostrictive system in accordance with claim 12, wherein the feedback configuration defines a centerline that is positioned between a nodal region and a loop region of the transducer.

15. The ultrasonic magnetostrictive system in accordance with claim 12, wherein the at least one distal coil in the feedback configuration includes n+i turns, wherein i is greater than 1, and wherein i increases as a distal end of the at least one distal coil approaches an end of the drive coil, and wherein a length of the feedback configuration is less than a length of the drive coil.

16. The ultrasonic magnetostrictive system in accordance with claim 12, wherein the feedback configuration includes at least two distal coils, wherein the number of turns on each distal coil is n/2+i turns, wherein i is in a range of 0 and n/2 turns, and wherein i increases as positions of the at least two distal coils approach an end of the drive coil, and wherein a length of the feedback configuration is less than a length of the drive coil.

17. The ultrasonic magnetostrictive system in accordance with claim 12, wherein the at least one distal coil in the feedback configuration includes n+i turns, wherein i is greater than 1, and wherein i increases as a distal end of the at least one distal coil approaches an end of the drive coil, wherein a length of the feedback configuration is less than a length of the drive coil, and wherein the at least one distal coil is positioned towards a free end of the transducer.

18. The ultrasonic magnetostrictive system in accordance with claim 12, wherein the drive coil is continuously wound in a single direction and contains at least one gap in its windings.

\* \* \* \* \*